(12) United States Patent
Sampath et al.

(10) Patent No.: US 6,596,858 B2
(45) Date of Patent: Jul. 22, 2003

(54) PROCESS FOR THE PRODUCTION OF 2-HALO-6-AMINOPURINE DERIVATIVES

(75) Inventors: UmaShanker Sampath, Ballwin, MO (US); Lawrence Bartlett, Bonne Terre, MO (US)

(73) Assignee: Reliable Biopharmaceutical, Inc., St. Louis, MO (US)

( * ) Notice: Subject to any disclaimer, the term of this patent is extended or adjusted under 35 U.S.C. 154(b) by 0 days.

(21) Appl. No.: 09/803,765

(22) Filed: Mar. 12, 2001

(65) Prior Publication Data

US 2002/0052492 A1 May 2, 2002

Related U.S. Application Data

(63) Continuation of application No. 09/274,518, filed on Mar. 23, 1999, now Pat. No. 6,252,061.
(60) Provisional application No. 60/079,059, filed on Mar. 23, 1998.

(51) Int. Cl.$^7$ ..................... C07H 19/167; C07H 19/173
(52) U.S. Cl. .................. 536/27.62; 536/27.11; 536/27.13; 536/27.14; 536/27.2; 536/27.6; 536/27.8; 544/264
(58) Field of Search ............... 536/27.11, 27.14, 536/27.63, 27.8, 27.81, 22.1, 27.1, 27.13, 27.2, 27.21, 27.6, 27.62; 544/264

(56) References Cited

U.S. PATENT DOCUMENTS

| | | | | |
|---|---|---|---|---|
| 4,719,295 A | * | 1/1988 | Cook et al. |
| 4,760,137 A | * | 7/1988 | Robins et al. |
| 5,185,444 A | * | 2/1993 | Summerton et al. |
| 5,208,327 A | * | 5/1993 | Chen |
| 5,217,866 A | * | 6/1993 | Summerton et al. |
| 5,382,580 A | * | 1/1995 | Chen et al. |
| 5,384,310 A | * | 1/1995 | Montgomery et al. |
| 5,506,351 A | * | 4/1996 | McGee |
| 5,571,902 A | * | 11/1996 | Ravikumar et al. |
| 6,252,061 B1 | * | 6/2001 | Sampath et al. |

FOREIGN PATENT DOCUMENTS

| | | |
|---|---|---|
| EP | 0 259 574 B1 | 3/1992 |
| EP | 0 490 818 A1 | 6/1992 |
| EP | 0 601 322 A3 | 6/1994 |
| JP | 7-118156 | 9/1995 |
| JP | 7-118288 | 9/1995 |

OTHER PUBLICATIONS

Robins et al., Can J. Chem., vol. 59, 1981.*
Robins et al., J. Am. Chem. Soc., vol. 103, pp. 932–933, 1981.*
Gerster et al., *Journal of the American Chemical Society* 87, 16: 3752–59 (Aug. 20, 1965).
Seela et al., *Helvetica Chimica Acta* 77: 622–30 (1994).
Worthington et al., *Carbohydrate Research* 275: 275–284 (1995).
Montgomery et al., *J. Med. Chem.* 12: 498–504 (May 1969).
Gerster et al., *J. Org. Chem.* 33, 3: 1070–73 (Mar. 1968).
Christensen et al., *J. Med. Chem.* 15, 7: 735–39 (1972).
Robins et al., *Can. J. Chem.* 59: 2601–07 (1981).
Kazimierczuk et al., *J. Am. Chem. Soc.* 106: 6379–82 (1984).
Huang et al., *J. Med. Chem.* 27: 800–02 (1984).
Weber et al., *Journal of Pharmaceutical Sciences* 525, 83, 4: 525–31 (Apr. 1994).
Wright et al., *J. Org. Chem.* 52: 4617–18 (1987).
Gerster et al., *J. Org Chem.* 31: 3258–62 (Oct. 1966).
March, *Advanced Organic Chemistry*, 3rd Edition: 647–48 (1985).
Robins et al., *Can. J. Chem.* 59 (17): 2608–11 (Sep. 1, 1981).
Nair et al., *J. Org. Chem.* 45 (20): 3969–74 (1980).
Nair et al., *Synthesis* 1982: 670–72 (Aug. 1982).
Cadogan et al., *Journal of the Chemical Society, Chemical Communications*: 851–852 (1976).
Robins et al., *Nucleic Acids Research Symposium Series* 9: 61–63 (Sep. 1981).
Wibert, K.B., *Laboratory Technique in Organic Chemistry*: 75, 99–110, 149, 151–165, McGraw–Hill (1960).

* cited by examiner

*Primary Examiner*—James O. Wilson
*Assistant Examiner*—Patrick Lewis
(74) *Attorney, Agent, or Firm*—Darby & Darby

(57) ABSTRACT

A novel process for preparing 2-halo-6-aminopurine derivatives and their analogs is disclosed. The method comprises halogenation of 2,6-diaminopurine derivatives at the C-2 position in a specific combination of aprotic polar and nonpolar organic solvents to give the corresponding halogenated derivatives.

2 Claims, No Drawings

PROCESS FOR THE PRODUCTION OF 2-HALO-6-AMINOPURINE DERIVATIVES

This application is a continuation of application Ser. No. 09/274,518 filed Mar. 23, 1999, now U.S. Pat. No. 6,252,061. This application claims priority under 35 U.S.C. §119 from provisional application Ser. No. 60/079,059, filed Mar. 23, 1998, the disclosure of which is incorporated herein in its entirety.

FIELD OF THE INVENTION

The invention relates to a novel process for preparing 2-halo-6-aminopurine compounds and derivatives thereof, comprising halogenation of 2,6-diaminopurine compounds at the C-2 position to give the corresponding halogenated compounds, including halogenated

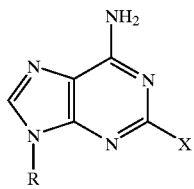

nucleosides. These nucleosides, e.g., 2-chloro-6-aminopurine-2'-deoxyribonucleoside, i.e., the compound with the above structure wherein R is 2'-deoxyribose and X is Cl (2-chloro-2'-deoxyadenosine), are useful as antileukemic agents, e.g., in treating leukemias such as hairy cell leukemia.

The invention also relates to methods for the synthesis of acyclic derivatives of 2-halo-6-aminopurines and 2-halo-6-aminopurine morpholino derivatives which are useful in the preparation of synthetic oligonucleotide analogs.

BACKGROUND OF THE INVENTION

Processes for preparing 2-chloro-6-aminopurine-2'-deoxyribonucleoside (2-chloro-2'-deoxyadenosine, hereinafter "2-CdA") and other 2-chloro-6-aminopurines are known in the art. Such processes are described in, e.g., U.S. Pat. No. 4,760,137; Kazimierzuk et al., J. Am. Chem. Soc., 106:6379, 1984; Wright et al., J. Org. Chem., 52:4617, 1987 and Christensen et al., J. Med. Chem., 15:735, 1972. The preparation of 2-CdA described by these workers requires the glycosylation of a dihalogenated purine to give an intermediate dihalogenated nucleoside which is then transformed into the desired nucleoside. More specifically, these workers described the glycosylation of 2,6-dichloropurine with 1-chloro-2'-deoxy-3',5'-di-O-p-toluyl-β-D-erythropentofuranose to give a mixture of N-7 and N-9 isomers of 2,6-dichloro-(2'-deoxy-3',5'-di-O-p-toluyl-β-D-erythropentofuranosyl)-purine. This process suffers from several shortcomings, such as the formation of isomeric side products at the 1'-carbon and the utilization of costly starting materials, such as 2,6-dichloropurine.

U.S. Pat. No. 5,208,327 discloses a method for preparation of 2-CdA from guanosine in eight steps via a 2-chloroadenosine intermediate in 2.8% overall yield (from guanosine). This method is inefficient and requires several protection and deprotection steps in order to remove the 2' hydroxyl to yield a 2'-deoxy product. The synthesis of the 2-chloroadenosine intermediate also disclosed in the same patent uses protecting group chemistry and an alternate halogenation/amination strategy. This process is extremely expensive because of the multiple steps involved and the use of expensive 2-chloroguanosine starting material, and is not suitable for truly large scale production.

Processes for the preparation of compounds of the formula:

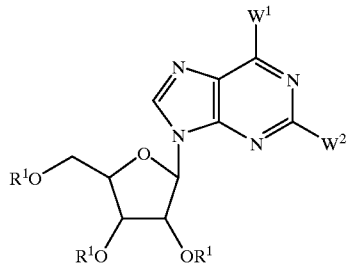

wherein $R^1$ is acyl or tolyl and $W^1$ and $W^2$ are independently halogen or amino from the corresponding per-O-protected nucleosides are disclosed, e.g., in Robins & Uznanski, Can. J. Chem. 59, 2601, 1981; Montgomery & Hewson, J. Med. Chem. 12, 498, 1969; and Huang et. al. J. Med. Chem., 27, 800–802, 1984. The transformation of the starting nucleosides to 2-halopurines requires several steps, including diazotization of the 2-amino intermediates in non-polar organic solvents, followed by halogenation. Thus, this method is completely unfeasible when it is necessary to utilize starting materials that are not soluble or only sparingly soluble in non-polar organic solvents, in contrast to the methods of the present invention, detailed below.

Methods for the conversion of unprotected purine ribonucleosides having the formula:

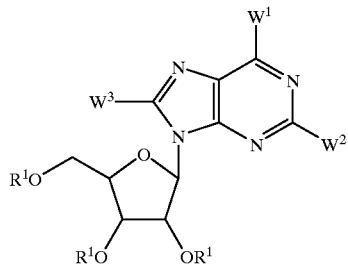

wherein $R^1$ is hydrogen, $W^3$ is halogen or hydrogen, and $W^1$ and $W^2$ are independently amino or halogen, to 2-halogenated nucleosides are known in the art (Gerster et. al., J. Org. Chem., 33, 1070, 1968; Gerster et. al., J. Org. Chem., 31, 3258, 1966; Gerster et. al., J. Am. Chem. Soc, 87, 3752, 1965). However, these methods provide low yields of products, and require reactions to be performed with sodium nitrite at temperatures below 0° C. in aqueous solution, thus making drying and separation of products difficult. The prior art also discloses that diazotization of 2-amino groups is only possible for ribonucleosides, because the reaction conditions cleave the glycosyl linkage of the corresponding deoxynucleosides (see Montgomery & Hewson, J. Med. Chem. 12, 498, 1969).

Thus, while the prior art discloses processes for the preparation of 2-CdA and other 2-halo-6-amino nucleosides and deoxynucleosides, these methods all have disadvantages, such as including a glycosylation reaction, or the need for a series of nucleoside hydroxyl protection/deprotection reactions, or the need to manipulate 2-halo-ribonucleosides or analogs at sub-zero temperatures using aqueous reaction conditions.

The present inventors have now surprisingly and unexpectedly discovered methods that make it possible to convert unprotected 2'- or 3'-deoxynucleosides, ribonucleosides or analogs to the corresponding 2-halo derivatives. Also discovered by the present inventors are methods for performing such transformations on unprotected nucleosides where the unprotected nucleosides are highly insoluble in non-polar organic solvents.

SUMMARY OF THE INVENTION

The present invention overcomes the difficulties and shortcomings of the prior art with regard to the synthesis 2-halo-6-aminopurine compounds and derivatives thereof and especially of 2-halogenated purine ribonucleosides and 2-halogenated-2'- and 3'-deoxy and 2' and 3'-substituted purine ribonucleosides. Disclosed herein are methods for producing 2-halo-6-aminopurine compounds and derivatives thereof and especially 2-halogenated-2'-deoxy purine nucleosides, 2-halogenated purine ribonucleosides, and 2' and 3'-substituted analogs thereof via halogenation at the 2 position in a unique organic solvent system at room temperature.

Thus, in one aspect the invention relates to methods for producing 2-halo-6-amino derivatives, comprising the steps of:

admixing a nonpolar aprotic organic solvent with a polar aprotic organic solvent to produce a solvent mixture;

dissolving in the solvent mixture a compound having the formula

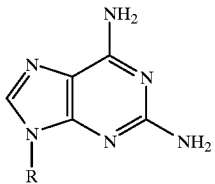

where R is selected from the group consisting of hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, a heterocyclic aryl group having from 1 to 20 carbon atoms and 1 to 10 heteroatoms, sugar moieties selected from the group consisting of β-D-ribofuranosyl, deoxy-β-D-furanosyl, xylofuranosyl, arabinofuranosyl, and 2'-, 3'-, and 2',3'-substituted or derivatized analogs of β-D-ribofuranosyl, deoxy-β-D-furanosyl, xylofaranosyl, and arabinofuranosyl sugar moieties; and reacting the compound in the solvent mixture with an organic nitrite and a metal halide, where the metal halide is a Lewis acid, to produce a reaction product.

In another aspect the invention relates to the methods for producing 2-halonucleosides comprising the steps of:

admixing a nonpolar aprotic organic solvent with a polar aprotic organic solvent to produce a solvent mixture;

dissolving in the solvent mixture a nucleoside having the formula

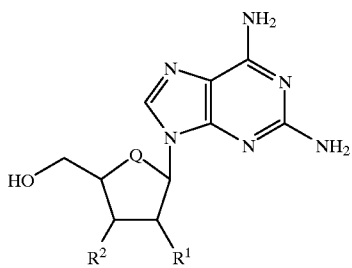

where Q is O or S;

where $R^1$ and $R^2$ together form a moiety with the formula O—A(Y)—O, where A is C, S, or P—R and where Y is O, S, N—R, or 2R;

or where $R^1$ and $R^2$ are independently hydrogen, O—R, R, N—$R_2$, $N_3$, X, or S—R;

where R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms and where X is Cl, Br, F, or I; and reacting the nucleoside in the solvent mixture with an organic nitrite and a metal halide, where the metal halide is a Lewis acid, to produce a reaction product.

In yet another aspect the invention relates to the methods for producing 2-halo-6-aminoalkyloxy derivatives comprising the steps of:

admixing a nonpolar aprotic organic solvent with a polar aprotic organic solvent to produce a solvent mixture;

dissolving in the solvent mixture a nucleoside analog having the formula

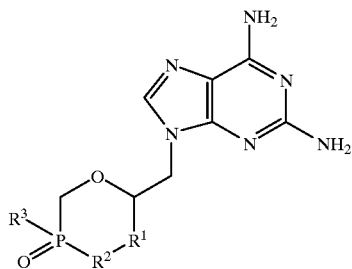

where $R^1$ is hydrogen, $CH_2OH$, or $CH_2OPOM$; $R^2$ is OH, OPh, or OPOM; and $R^3$ is OH, OPh, or OPOM;

or where $R^1$ and $R^2$ form the moiety —$CH_2O$— and $R^3$ is OH, wherein POM is pivalyloxymethyl; and reacting the nucleoside analog in the solvent mixture with an organic nitrite and a metal halide, where the metal halide is a Lewis acid, to produce a reaction product.

In one particular aspect, the invention relates to methods for producing 2-halo-6-aminopurine-2'-deoxy or 2'-substituted nucleosides comprising the steps of:

admixing a nonpolar aprotic organic solvent with a polar aprotic organic solvent to produce a solvent mixture;

dissolving in the solvent mixture an unprotected nucleoside having the formula

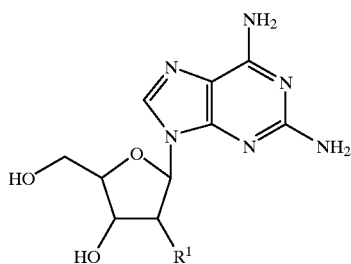

where $R^1$ is hydrogen, OR, R, $NR_2$, $N_3$, X, or SR; R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

In another aspect, the invention relates to methods for producing 2-halo-6-aminopurine-3'-deoxy or 3'-substituted nucleosides comprising the steps of: admixing a nonpolar aprotic organic solvent with a polar aprotic organic solvent to produce a solvent mixture;

dissolving in the solvent mixture an unprotected nucleoside having the formula

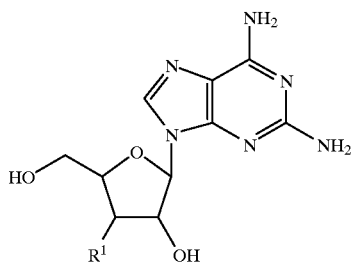

where $R^1$ is hydrogen, OR, R, $NR_2$, $N_3$, X, or SR; R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, wherein the metal halide is a Lewis acid, to produce a 2-halo-6-aminopurine reaction product.

In a further aspect, the present method comprises a method for stabilizing the 2-haloadenosine and 2-halodeoxyadenosine reaction products produced by the synthetic methods of the present invention comprising subjecting the reaction products to resin column chromatography.

In another aspect, the invention relates to methods for producing 2-halo-6-aminopurine-2',3'-dideoxy nucleosides comprising the steps of: admixing a nonpolar aprotic organic solvent with a polar aprotic organic solvent to produce a solvent mixture;

dissolving in the solvent mixture an unprotected nucleoside having the formula

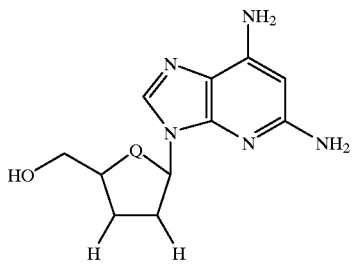

where Q is O or S; and reacting the unprotected nucleoside in the solvent mixture with an organic nitrite and a metal halide, wherein the metal halide is a Lewis acid, to produce a 2-halo-6-aminopurine reaction product.

Another aspect the invention relates to the methods for producing 2-halo-6-aminopurine-4-thionucleosides comprising the steps of:

admixing a nonpolar aprotic organic solvent with a polar aprotic organic solvent to produce a solvent mixture;

dissolving in the solvent mixture a 4-thionucleoside having the formula

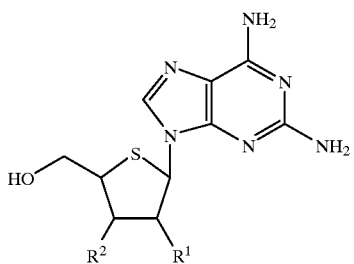

where $R^1$ and $R^2$ are independently hydrogen, OR, R, $NR_2$, $N_3$, X, or SR;

where R is linear or branched chain alkyl, cycloalkyl, alkoxyalkyl, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the nucleoside in the solvent mixture with an organic nitrite and a metal halide, where the metal halide is a Lewis acid, to produce a reaction product.

Yet another aspect the invention relates to the methods for producing 2-halo-6-aminopurine-2',3'-derivatized nucleosides comprising the steps of:

admixing a nonpolar aprotic organic solvent with a polar aprotic organic solvent to produce a solvent mixture;

dissolving in the solvent mixture a nucleoside having the formula

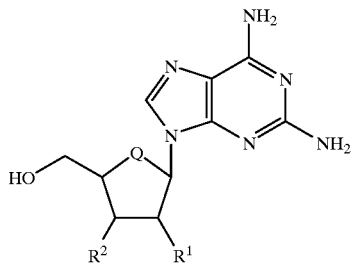

where Q is O or S;
where $R^1$ and $R^2$ together form a moiety with the formula O—A(Y)—O, where A is C, S, or P—R and where Y is O, S, N—R, or 2R;
or where $R^1$ and $R^2$ are independently hydrogen, O—R, R, N—$R_2$, $N_3$, X, or S—R; where R is linear or branched chain alkyl cycloalkyl, alkoxyalkyl, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I;

reacting the nucleoside in the solvent mixture with an organic nitrite and a metal halide, where the metal halide is a Lewis acid, to produce a reaction product.

In one particular aspect, the invention relates to methods for producing 2-halo-6-aminopurine-2'-deoxy or 2'-substituted N-7 glycosylated nucleosides comprising the steps of:

admixing a nonpolar aprotic organic solvent with a polar aprotic organic solvent to produce a solvent mixture;

dissolving in the solvent mixture an unprotected N-7 glycosylated nucleoside having the formula

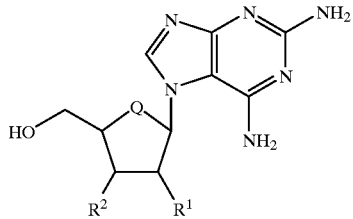

where Q is O or S;
where $R^1$ and $R^2$ together form a moiety with the formula O—A(Y)—O, where A is C, S, or P—R and where Y is O, S, N—R, or 2R;
or where $R^1$ and $R^2$ are independently hydrogen, O—R, R, N—$R_2$, $N_3$, X, or S—R;
where R is linear or branched chain alkyl, cycloalkyl, alkoxyalkyl, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

In yet another aspect, the present invention is directed to novel morpholino 2-halopurines of the formula:

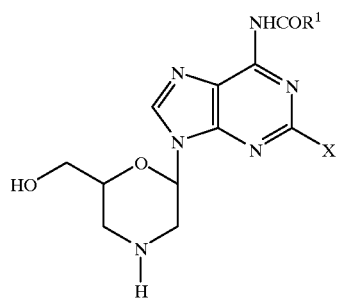

where X is fluorine, chlorine, bromine, or iodine and $R^1$ is alkyl, aryl, substituted aryl, aryloxy, or substituted aryloxy, and methods for synthesizing such compounds.

DETAILED DESCRIPTION OF THE INVENTION

All patents, patent applications, and literature references cited herein are incorporated by reference in their entirety. In case of a conflict in terminology, the present specification controls.

Definitions

The following terms generally have the following meanings.

The term "aryl" refers to aromatic groups, which have at least one ring having a conjugated pi electron system, including for example carbocyclic aryl, heterocyclic aryl and biaryl groups, all of which may be optionally substituted. Carbocyclic aryl groups are groups wherein all the ring atoms on the aromatic ring are carbon atoms, such as phenyl. Also included are optionally substituted phenyl groups, being preferably phenyl or phenyl substituted by one to three substituents. Further included are phenyl rings fused with a five or six membered heterocyclic aryl or carbocyclic ring, optionally containing one or more heteroatoms such as oxygen, sulfur, or nitrogen. Where chemical groups or moieties are indicated to be "optionally substituted", it is meant that the groups can be chemically bonded to one or more other chemical groups, such groups preferably being, but not limited to, lower alkyl, hydroxy, lower alkoxy, lower alkanoyloxy, halogen, cyano, perhalo lower alkyl, lower acylamino, lower alkoxycarbonyl, amino, alkylamino, carboxamido, and sulfamido.

Heterocyclic aryl groups are monocyclic or polycyclic groups having from 1 to 10 heteroatoms as ring atoms in the aromatic rings and the remainder of the ring atoms carbon atoms. Suitable heteroatoms include oxygen, sulfur, and nitrogen. Heterocyclic aryl groups include furanyl, thienyl, pyridyl, pyrrolyl, pyrimidyl, pyrazinyl, imidazolyl, and the like, all optionally substituted.

Optionally substituted furanyl represents 2- or 3-furanyl or 2- or 3-furanyl preferably substituted by lower alkyl or halogen. Optionally substituted pyridyl represents 2-, 3- or 4-pyridyl or 2-, 3- or 4-pyridyl preferably substituted by lower alkyl or halogen. Optionally substituted thienyl represents 2- or 3-thienyl, or 2- or 3-thienyl preferably substituted by lower alkyl or halogen.

The term "aralkyl" refers to an alkyl group substituted with an aryl group. Suitable aralkyl groups include benzyl, picolyl, and the like, and may be optionally substituted.

The term "lower" referred to herein in connection with organic radicals or compounds respectively defines such with up to and including 7, preferably up to and including 4 and advantageously one or two carbon atoms. Such groups may be straight chain or branched.

The terms (a) "alkylamino", (b) "arylamino", and (c) "aralkylamino", respectively, refer to the groups —NRR' wherein respectively, (a) R is alkyl and R' is hydrogen, aryl or alkyl; (b) R is aryl and R' is hydrogen or aryl, and (c) R is aralkyl and R' is hydrogen or aralkyl.

The term "acylamino" refers to RC(O)NR'.

The term "carbonyl" refers to —C(O)—.

The term "acyl" refers to RC(O)— where R is alkyl, aryl, aralkyl, or alkenyl.

The term "carboxamide" or "carboxamido" refers to —CONRR wherein each R is independently hydrogen, lower alkyl or lower aryl.

The term "alkyl" refers to saturated aliphatic groups including straight-chain, branched chain and cyclic groups, optionally containing one or more heteroatoms.

The invention in one aspect relates to a novel process for preparing the compound 2-CdA and other 2-halogenated purine nucleosides and 2-halogenated 2'-deoxy and 2' substituted nucleosides having the formula:

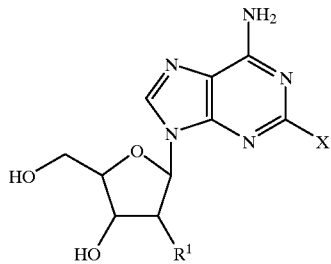

where $R^1$ is hydrogen, OR, R, $NR_2$, $N_3$, X, or SR; R is hydrogen, $C_1$ to $C_{20}$ alkyl, including linear and branched chain alkyl and cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I.

The method comprises admixing a nonpolar aprotic organic solvent with a polar aprotic organic solvent to produce a solvent mixture, dissolving or suspending in the solvent mixture an unprotected nucleoside having the formula:

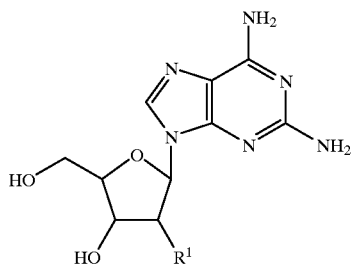

where $R^1$ is hydrogen, OR, R, $NR_2$, $N_3$, X, or SR; R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

Methods for the synthesis of the 2'-deoxy, 2'-OH, and 2'-O-alkyl nucleoside diaminopurine starting materials are known in the art. Syntheses of many exemplary starting materials are described in such works as: Chemistry of Nucleosides and Nucleotides, Vol. 1, Ed. Townsend, L. B., Plenum Press, New York, N.Y., 1988; Chemistry of Nucleosides and Nucleotides, Vol 2., Ed. Townsend, L. B., Plenum Press, New York, N.Y., 1991; Chemistry of Nucleosides and Nucleotides, Vol. 3, Ed. Townsend, L. B., Plenum Press, New York, N.Y., 1994; Oligonucleotide Synthesis: A Practical Approach, Ed. Gait, M. J., Oxford Univ. Press, New York, N.Y., 1984; Oligonucleotides and Analogues: A Practical Approach, Ed. Eckstein, F., Oxford Univ. Press, New York, N.Y., 1991. Syntheses of such starting materials are also described, e.g., in U.S. Pat. Nos. 5,506,351 and 5,571,902.

Methods for the synthesis of 2'-fluoro and other 2'-haloribonucleosides (i.e., where $R^1$ is halogen) are described in, e.g., U.S. Pat. No. 5,420,115, European Patent application 417999; Tuttle, J. V.; Tisdale, S. M. and Krenitsky, T. A., J. Med. Chem., 36(1): 119–125, 1993; Thomas, H. J.; Tiwari, K. N.; Clayton, S. J.; Secrist, J. A. III and Montgomery, J. A., Nucleosides and Nucleotides, 13 (1–3): 309–323, 1994. Starting materials for the synthesis of compounds of the invention where $R^1$ is $N_3$ can be obtained by substitution of 2'-halo nucleosides. Starting materials for the synthesis of compounds of the invention where $R^1$ is NH—R can be obtained by reduction of these $N_3$ compounds.

In a preferred embodiment, X is bromine, chlorine, fluorine, or iodine, and $R^1$ is hydrogen.

In other preferred embodiments, X is bromine, chlorine, fluorine, or iodine, and $R^1$ is hydroxyl or is OR, where R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms.

In a most preferred embodiment, X is chlorine and $R^1$ is hydrogen.

In another aspect, the invention is directed to methods for synthesizing 2-halogenated purine 3'-O-alkyl, 3'-deoxy, and 3'-substituted ribonucleosides. The methods comprise admixing a nonpolar aprotic organic solvent with a polar aprotic organic solvent to produce a solvent mixture, dissolving or suspending in the solvent mixture an unprotected nucleoside having the formula:

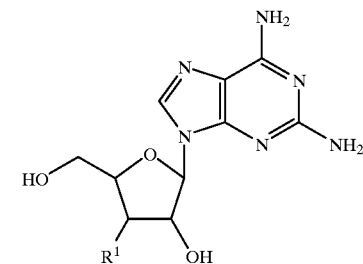

where $R^1$ is hydrogen, OR, R, $NR_2$, $N_3$, X, or SR; R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

Methods for the synthesis of 3'-O-alkyl starting materials are known and widely reported in the art and are described, e.g., in U.S. Pat. No. 5,506,351. The synthesis of unprotected 3'-deoxyribonucleoside is set out in Kumar, A.; Khan, S. I.; Manglani, A.; Khan, Z. K. and Katti, S. B., Nucleosides & Nucleotides 13(5): 1049–1058, 1994. Methods for the synthesis of 3'-substituted nucleosides, e.g., 3'-Fluoro-3'-deoxyribonucleoside are described in Koshida, R.; Cox, S.; Harmenberg, J.; Gilljam, G. and Wahren, B., Antimicrob. Agents Chemother., 33(12): 2083–2088, 1989. Exemplary methods for the synthesis of other 3'-substituted nucleosides, such as 3'-Amino-3'-deoxyribonucleoside are set forth in Kissman, H. M.; Hoffman, A. S.; Weiss, M. J. J. Med. Chem. 6(4): 407–409, 1963; Goldman, L.; Marsico, J. W.; Weiss, M. J. J. Med. Chem. 6(4): 410–412, 1963; Goldman, L.; Marsico, J. W.; J. Med. Chem. 6(4), 413–423, 1963; Soenens, J.; Francois, G.; Van den Eeckhout, E.; Herdewijn, P., Nucleosides & Nucleotides 14(3–5): 409–411, 1995; and Pannecouque, C.; Van Poppel, K.; Balzarini, J.; Claes, P.; De Clercq, E.; Herdewijn, P., Nucleosides & Nucleotides 14(3–5): 541–544, 1995).

Methods for the halogenation of 2,6 diaminonucleosides coupled to sugar moieties such as arabinose and xylose are also within the scope of the present invention. Exemplary syntheses of such starting materials can be found, e.g., in Montgomery, J. A. and Hewson, K., J. Med. Chem., 12: 498–504, 1969; Hansske, F.; Madej, D. and Robins, M. J., Tetrahedron, 40(1): 125–135, 1984 (xylose and arabinose); Krenitsky, T. A., Koszalka, G. W.; Tisdale, J. V.; Rideout, J. L. and Elion, G. B., Carbohydr. Res., 97(1): 139–146, 1981; Krenitsky, T. A., Elion, G. B. and Rideout, J. E., EP 790613; Utagawa, T.; Miyoshi, T.; Morisawa, H.; Yamazaki, A.; Yoshinaga, F. and Mitsugi, K., DE 2835151; Elion, G. B. and Strelitz, R. A., U.S. Pat. No. 4,038,479; Wellcome Foundation, GB 1,386,584; Elion, G. B.; Litster, J. E. and Beachamp, L. M. III, DE 2156637; Elion, G. B. and Strelitz, R. A., DE 205637. Exemplary syntheses of 2'-substituted arabinonucleoside starting materials can be found in, e.g., Robins, M. J.; Zou, R.; Hansske, F. and Wnuk, S. F., Can. J. Chem. 75(6): 762–767, 1997; Watanabe, K. A.; Pankiewicz, K. W.; Krzeminski, J. and Nawrot, B., WO 9211276A1; Tuttle, J. V. and Krenitsky, T. A., EP 285432A2; Watanabe, K. A.; Chu, C. K. and Fox, J. J., EP 219829A2; and Montgomery, J. A.; Shortnacy, A. T.; Carson, D. A. and Secrist, J. A. III, J. Med. Chem., 29(11): 2389–2392, 1986.

Methods for synthesizing 2-halogenated purine 2',3'-dideoxy nucleosides comprise admixing a nonpolar aprotic organic solvent with a polar aprotic organic solvent to produce a solvent mixture, dissolving or suspending in the solvent mixture an unprotected nucleoside having the formula

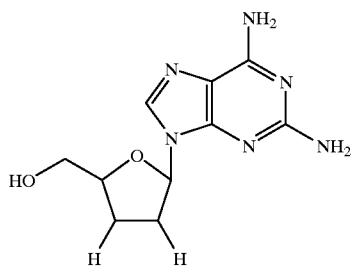

and reacting the unprotected nucleoside in the solvent mixture with an organic nitrite and a metal halide, where the metal halide is a Lewis acid, to produce a reaction product.

Such starting compounds can be prepared according to well-known methods of dideoxy nucleoside syntheses such as those disclosed by Webb II, R. R.; Wos, J. A.; Martin, J. C.; Brodfuehrer, P. R. Nucleosides & Nucleotides, 7(2): 147–153, 1988; Prisbe, E. J.; Martin, J. C. Synth. Comm. 15(5): 401–409 1985; Horwitz, J. P.; Chua, J.; Da Rooge, M. A.; Noel, M.; Klundt, I. L. J. Org. Chem. 31: 205–211, 1966; Horwitz, J. P.; Chua, J.; Noel, M.; Donatti, J. T. J. Org. Chem. 32: 817–818, 1967.

Methods for synthesizing 2-halo 6-aminopurine-4'-thionucleosides comprise admixing a nonpolar aprotic organic solvent with a polar aprotic organic solvent to produce a solvent mixture, dissolving or suspending in the solvent mixture an unprotected nucleoside having the formula

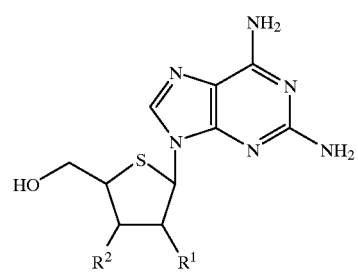

where $R^1$ and $R^2$ are independently hydrogen, OR, R, $NR_2$, $N_3$, X, or SR; where R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

Such starting materials can be prepared according to well-known methods for 4-thionucleosides synthesis, such as those disclosed in Leydier, C.; Bellon, L.; Barascut, J. -L.; Imbach, J. -L. Nucleosides & Nucleotides, 14(3–5): 1027–1030, 1995; Bellon, L.; Leydier, C.; Barascut, J. -L.; Imbach, J. -L. Nucleosides & Nucleotides 12(8): 847–852, 1993, Bellon, L.; Barascut, J. -L.; Imbach, J. -L. Nucleosides & Nucleotides 11(8): 1467–1479, 1992; and Reist, E. J.; Gueffroy, D. E.; Goodman, L. Chem. Ind. (London), 1364, 1964.

Methods for synthesizing 2-halo 6-aminopurine-2',3'-derivatized ribonucleosides comprise admixing a nonpolar aprotic organic solvent with a polar aprotic organic solvent to produce a solvent mixture, dissolving or suspending in the solvent mixture an unprotected nucleoside having the formula

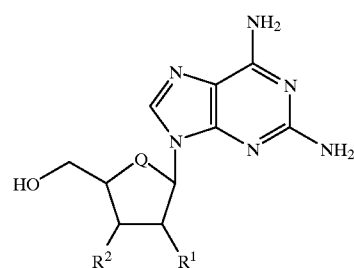

where Q is O or S; where $R^1$ and $R^2$ together form a moiety with the formula O—A(Y)—O, where A is C, S, or P—R and where Y is O, S, N—R, or 2R; where R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

Starting compounds for such methods, such as isopropylidene nucleosides, can be prepared based upon the methods described in, e.g., Schmidt, O. Th. Methods Carbohydr. Chem., II, 318 (1963); de Belder, A. N. Adv. Carbohydr. Chem. 20: 219, (1965); Hampton, A. J. Amer. Chem. Soc., 83: 3640, 1961; Davis, J. T.; Tirumala, S.; Jenssen, J. R.; Radler, E.; Fabris, D. J. Org. Chem., 60: 4167, 1995; Chladek, S.; Smrt, J. Collect. Czech. Chem. Commun. 28: 1301–1308, 1963; and Anzai, K.; Matsui, M. Bull. Chem. Soc. Jpn. 47: 417–420, 1974. Exemplary syntheses of 2'3'thionocarbonate nucleosides are described, e.g., in Anzai, K.; Matsui, M. Agric. Biol. Chem. 37: 345–348, 1973.

Methods for halogenation of 2,6 diaminonucleosides coupled to sugar derivatives at the N-7 position of the base comprise admixing a nonpolar aprotic organic solvent with a polar aprotic organic solvent to produce a solvent mixture, dissolving or suspending in the solvent mixture an unprotected nucleoside having the formula.

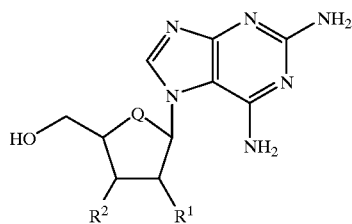

where $R^1$ and $R^2$ are independently hydrogen, OR, R, $NR_2$, $N_3$, X, SR; where Q is O or S; where R is hydrogen, $C_1$ to $C_{20}$ alkyl, including linear and branched chain alkyl, cycloalkyl, alkoxyalkyl, alkylamino, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and reacting the unprotected nucleoside in the solvent mixture with an organic nitrite and a metal halide, where the metal halide is a Lewis acid, to produce a reaction product.

Starting materials having the formula above are known, and can be prepared, e.g., according to the methods set out in Worthington, V. L., Fraser, W., and Schwalbe, C. H.; Carbohydrate Research, 275: 275–284, 1995. N-7 to N-9 or N-9 to N-7 glycosyl transfer reactions are described in the art, e.g., see Seela, F.; Winter, H. Nucleosides & Nucleotides, 14(1&2): 129–142, 1995.

The synthesis of 2-halo-6-aminopurines that have acyclic moieties linked at the N-9 position of the base comprise admixing a nonpolar aprotic organic solvent with a polar aprotic organic solvent to produce a solvent mixture, dissolving or suspending in the solvent mixture an unprotected diaminopurine that has an acyclic moiety linked at the N-9 position of the base, and reacting the unprotected compound in the solvent mixture with an organic nitrite and a metal halide, where the metal halide is a Lewis acid, to produce a reaction product.

Synthesis of diaminopurines that have an acyclic moiety linked at the N-9 position are well-known by those of ordinary skill in the art, and are described, e.g., by Holy, A. and Dvorakova, H., Nucleosides & Nucleotides 14(3–5): 695–702, 1995; Holy, A.; Dvorakova, H and Masojidkova, M., Collect. Czech. Chem. Commun., 60(8): 1390–1409, 1995; Holy, A.; Dvorakova, H.; de Clercq, E.; Desire, A. and Balzarini, J. M. H., WO 9403467; Rosenberg, I. and Holy, A.; Dvorakova, H., Collect. Czech. Chem. Commun., 54(8): 2190–2210, 1989; de Clercq, E.; Holy, A. and Rosenberg, I., Antimicrob. Agents Chemother., 33(2): 185–191, 1989; Yokota, T.; Mochizuki, S.; Konno, K.; Mori, S.; Shigeta, S. and de Clercq, E., Nucleic Acids Symposium Series 22, 17–18, 1990; Holy, A.; Rosenberg, I.; Dvorakova, H. and de Clercq, E., Nucleosides & Nucleotides 7(5–6): 667–670, 1988; Holy, A., Collect. Czech. Chem. Commun., 58(3): 649–674, 1993; Holy, A.; Rosenberg, I. and Dvorakova, H., Collect. Czech. Chem. Commun., 54(9): 2470–2501, 1989; Holy, A. and Rosenberg, I., CS 263955; Holy, A.; Rosenberg, I. and de Clercq, E., EP 253412; and Alexander, P. and Holy, A., Collect. Czech. Chem. Commun., 58(5): 1151–1163, 1993.

Scheme 1, below, sets forth an exemplary process of the present invention, the preparation of 2-CdA. The process utilizes 2,6-diamino purine deoxyriboside (2-amino deoxyadenosine or "DAPD") as a starting material. DAPD can be prepared by methods reported in U.S. Pat. No. 5,506,351 and in Seela and Gabler, Helv. Chim. Acta., 77: 622, 1994. DAPD is also commercially available from Reliable Biopharmaceutical Corporation, St. Louis, Mo.

SCHEME 1

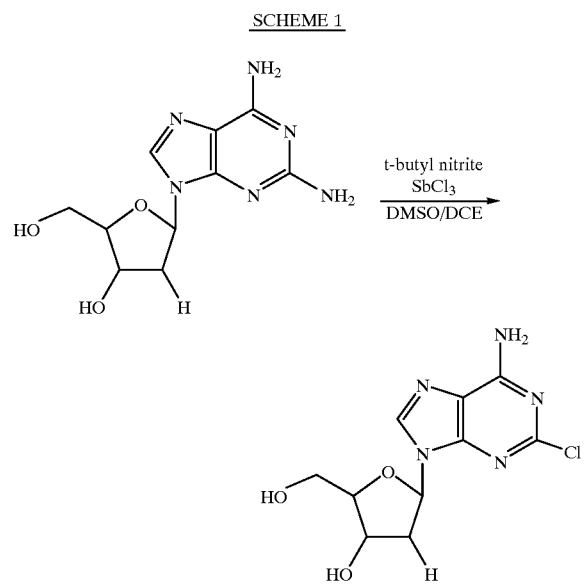

DAPD is suspended in a novel solvent combination which includes a polar aprotic organic solvent and a nonpolar aprotic organic solvent, (DMSO/dichloroethane is shown in Scheme 1), in a ratio of from about 1:10 to 10:1, and is cooled to 0° C. under an inert atmosphere, e.g., nitrogen or argon. Following the cooling step, the DAPD is diazotized at the 2-position with an organic nitrite, e.g., tert-butyl nitrite, and halogenated with a metal halide Lewis acid, e.g., antimony trichloride, at room temperature. The reaction produces 2-CdA in high yield. The reaction is unlike any other reactions for diazotization/substitution at the 2 position of a 2-amino purine nucleoside or 2-amino-2'-deoxy purine nucleoside because the diazotization is performed on a unprotected nucleoside. It is the selective combination of solvents in a particular ratio that allows the diazotization to proceed; the diazotization is a key step in this transformation. If only a polar aprotic organic solvent is used in the method, the diazotization reaction does not occur. Similarly, if only a nonpolar aprotic organic solvent is used in the method, the diazotization reaction fails. The chloride transfer, which employs metal halide Lewis acids, such as $SbCl_3$, is very efficient.

As indicated above, the role of the solvent in the halogenation reaction has been found to be critical. A series of $TBN/SbCl_3$ chlorination reactions using a number of aprotic polar organic solvents and non-polar organic solvents with varying solvent ratios were performed. It was determined that the reaction proceeds when the ratio of aprotic polar organic solvent to non-polar organic solvent is between 10:1 and 1:10. The preferred solvent ratio is 1 part aprotic polar organic solvent to 4 parts non-polar organic solvent. The reaction will not proceed when 100% non-polar solvent is used, nor will the reaction proceed when 100% aprotic polar organic solvent is used. Thus, the present inventors have discovered that there is a specific combination of solvents in a particular solvent component ratio range that is required for a successful halogenation reactions.

After the diazotization/substitution reaction is complete the reaction mixture is typically dried, using, e.g., a rotary evaporator, and neutralized. Subsequently, the crude product should immediately be stabilized by chromatography over a DVB (divinylbenzene)-cross-linked polystyrenic resin column, e.g., Amberchrom CG161 (Rohm & Haas, Philadelphia, Pa.). If this product-stabilizing column chromatography step is not performed, and the crude reaction mixture is stored, even at 0° C., the product will degrade over a period of about two days. The stabilized product can be further purified by subjecting it to a strong cation exchange resin column chromatography step, e.g., Dowex, (available from many commercial suppliers, such as Sigma Chemical, St. Louis, Mo. or Supelco, Bellefonte, Pa.) and the pure product, e.g., 2-CdA, can then be recrystallized from water.

The Amberchrom CG161 XUS resin column is prepared, typically so that about 4 g of 2-CldA per L of resin is applied. Two-thirds of the resin is removed from the column and slurried with the reaction mixture and then loaded onto the column. The column is washed with water at a flow rate of about 30 to about 80 mL/min until the absorbance at 265 nm drops below about 5 or until the 2-CldA begins to elute off the column and then 3 to 6 L fractions are collected. This is followed with elution with 5% methanol in water, and then 30% methanol in water until the absorbance of the eluate at 265 nm is below 10. All fractions containing greater than 75% 2Cl-dA by peak area using HPLC are collected and concentrated on a rotary evaporator at 45° C. The collected fractions are concentrated to a gum, which is at a stable state and can be left for up to 7 days if necessary.

The gum is dissolved in water and then concentrated to a concentration of 12–15 g of 2-CldA/L. This solution is then charged onto a Dowex 1×4 anion exchange resin column. The column is eluted at about 140–240 mL/min, first with water until the absorbance of the eluate at 265 nm is below 10, followed by 10% methanol in water, 15% methanol in water, and finally a 25% methanol in water wash until all of the 2-CldA has eluted off the column. Fractions of about 2–6 L each containing 2-CldA are collected and assayed for purity by HPLC. The fractions that contain >90% pure 2Cl-dA (by HPLC) is adjusted to pH 7.5 or greater by using 1.0M sodium bicarbonate solution to achieve a concentration 10 mM sodium bicarbonate. These are saved individually, without pooling. A second Dowex 1×4 anion exchange resin column is prepared, with about 1 L of resin per 10 g of 2-CldA. The column is equilibrated in 10 mM sodium bicarbonate solution before the 2-CldA charge is loaded. The charge is made up of the fractions from the previous 1×4 column. The fractions are loaded onto the 1×4 column in the order that they eluted off the first 1×4 column. After the column is loaded, the first eluant, 10 mM sodium bicarbonate in water, is started over the column. Once the majority of the 2-CldA is eluted off the column, the buffer is switched to 10% methanol in a 10 mM sodium bicarbonate solution. The column is washed with this eluant until 90% or more of 2-CldA has eluted off the column. All fractions that contain 2-CldA at greater than 98% purity by HPLC are concentrated in a rotary evaporator at 45° C. under vacuum.

The main (>98% pure) product pool is evaporated to a concentration of about 22 g 2-CldA per liter. The concentrated pool is filtered using a Buchner funnel and Whatman 54 hardened filter paper. The filtered solution is sealed and placed in a refrigerator for 17 hours at about 8 to 14° C. for crystallization. The concentrated solution should remain at about 8 to 14° C. for at least 14 hours. The crystallized 2-CldA is collected by filtration. The solids are washed with about 50 to 150 mL of cold water, i.e, at from about 5 to 10° C. Both the solids and the filtrate are assayed for 2-CldA using HPLC.

The crystallized solids are redissolved in 10 mM sodium bicarbonate solution at approximately 4 to 5 grams of 2-CldA per liter and then concentrated down to about 22 grams per liter using the rotary evaporator. The concentrated solution is then filtered and placed in a refrigerator for about 17 hours, or overnight for recrystallization. After about 17 hours, or overnight, the solids are filtered and both the solids and filtrate are assayed by HPLC.

If there is a significant amount of 2-CldA in the filtrate from the final recrystallization which is greater than 99% purity by HPLC, then the filtrate is concentrated and recrystallized to recover 2-CldA. All the product is 99% or greater pure is placed in a vacuum oven at a temperature of between about 37° and 45° C. for about 24 hours to dry. After drying the crystals are ground up and dried until the water content is about 2% or less by weight. The crystals are weighed for a final yield.

For maximum recovery, fractions with <98% pure 2-CldA from the second Dowex column are pooled and reprocessed over another 1×4 Dowex column. These clean [>98%] fractions are combined with the filtrates from previous recrystallizations. This solution is concentrated and recrystallized as described.

The product can be analyzed by any of the common structural analysis methods familiar to those of skill in the art, such as nuclear magnetic resonance (NMR), ultraviolet (UV), or infrared (IR) spectroscopy, or by elemental analysis and optical rotation. The overall yield of 2-CdA from DAPD achievable by the methods of the present invention is approximately ten fold (1000%) greater than obtained by the methods reported in the prior art, e.g., U.S. Pat. No. 5,208,327. Thus, the methods of the present invention are clearly superior in yield and simplicity relative to the methods disclosed by the prior art.

The improved methods of the present invention also permit the synthesis of novel 2-halo-6-aminopurine morpholino compounds. These morpholino compounds are useful in, e.g., synthesizing polymers which can bind specifically to polynucleotides with specific sequences. Thus, they are useful for the detection of specific sequences of polynucleotides, and are potentially useful as inactivators of specific genetic sequences.

The novel 2-halo-6-aminopurine morpholino compounds of the invention have the formula:

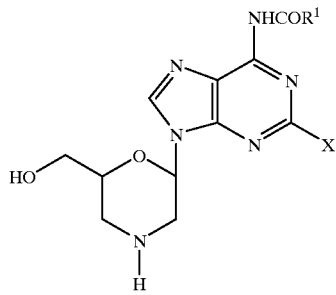

where X is F, Cl, Br, or I and where $R^1$ is aryl, alkyl, aklyoxy or aryloxy. The novel morpholino compounds of the invention can be prepared, e.g., according to Scheme 2, below.

SCHEME 2

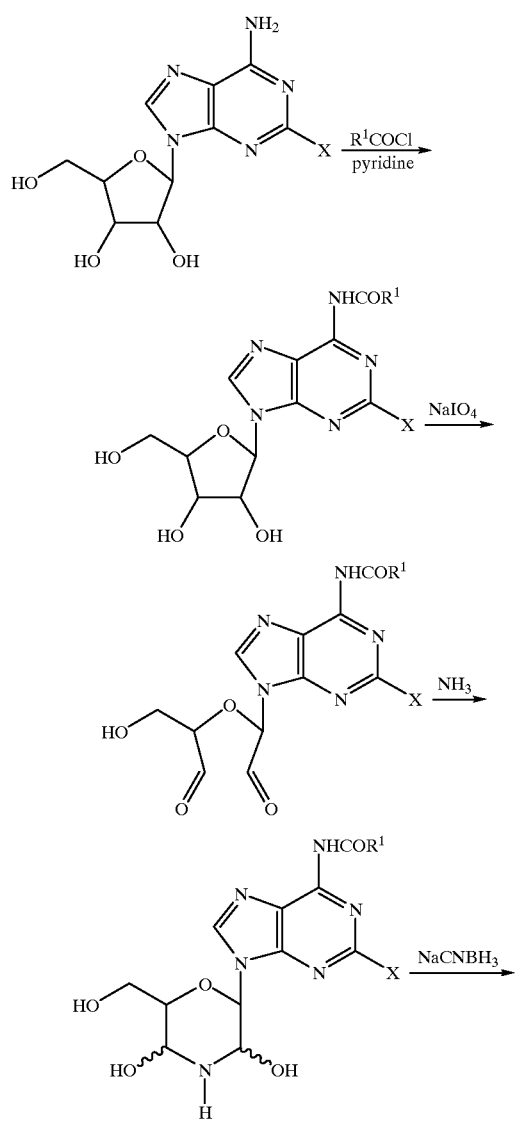

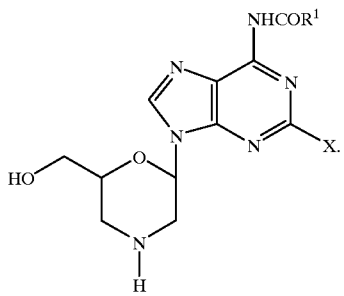

A 2-amino-6-halopurine nucleoside, prepared according to the methods disclosed above and in the Examples, below, is first N-protected with a carboxylic acid chloride and this intermediate is treated with sodium periodate, which cleaves the ribose sugar ring between the 2' and 3' carbons, yielding a dialdehyde. The dialdehyde is reacted with ammonia, which results in a morpholino ring having 2' and 3' hydroxyl groups. Sodium cyanoborohydride treatment reduces the ring hydroxyl groups, yielding the novel morpholino compounds of the invention. The synthesis of other morpholinopurines are disclosed, e.g., in U.S. Pat. Nos. 5,185,444 and 5,521,063.

The following non-limiting examples are provided to illustrate the invention. Modifications and variations of the methods and compounds disclosed herein will be apparent to those of ordinary skill in the art, and are intended to be within the scope of the invention.

EXAMPLE 1

Synthesis of 2-chloro-2'deoxyadenosine

To a three-neck 12 L reaction flask equipped with a stir bar, temperature probe, and drying tube was added dry diaminopurine deoxyriboside (DAPD, 60 g, 0.225 mol) and 900 ml DMSO. The mixture was stirred until the DAPD dissolved completely and then dichloroethane (4200 ml) was added. The solution was cooled to below 10° C. using an ice bath and then antimony trichloride (24 g, 0.105 mol) was added. To the reaction mixture was then added tert-butyl nitrite (55.4 mL, 48 g, 0.466 mol) dropwise over 10 minutes. After 20 minutes stirring, a second aliquot of antimony trichloride (24 g, 0.105 mol) was added, followed by a final third aliquot of antimony trichloride (24 g, 0.105 mol) after an additional 20 minutes. The reaction was stirred overnight at room temperature. When less than 5% diaminopurine deoxyriboside (by peak area using HPLC [Novapak C-18; 5% acetonitrile/water, 0.1M TEA, pH 7 with acetic acid]) remained, the reaction was quenched with ~102 mL triethylamine in approximately 35 mL aliquots until the pH was 7. The reaction mixture was evaporated at 40° C. under reduced pressure to dryness, placed in an ice bath, stirred vigorously and treated slowly with 3200 mL of 0.1M sodium bicarbonate solution.

EXAMPLE 2

Stabilization and isolation of 2-chloro-2'-deoxyadenosine

The neutralized reaction mixture was immediately applied to a polystyrene-divinylbenzene crosslinked polymeric resin column (Amberchrom CG161 md, 2500 g) to prevent product degradation. The column was eluted with water, 5% MeOH/water and 30% MeOH/water and the collected fractions were analyzed. Fractions containing >75% 2-CdA were pooled and concentrated to dryness. The crude product residue from the Amberchrom column was dissolved in water and loaded on a polystyrene anion exchange resin (Dowex 1×4 200–400 mesh, 500 ml) column. The column was eluted with water, 10% MeOH/water, 15% MeOH/water and 25% MeOH/water, and the eluate was collected from the column in fractions was analyzed by HPLC [Novapak C-18; 5% acetonitrile]. The fractions containing >90% 2-CdA were pooled and concentrated to dryness. The crude product residue from the first Dowex column was dissolved in water and loaded on a second polystyrene anion exchange resin (Dowex 1×4 200–400 mesh, 2000 ml) column. This second Dowex column was eluted with water until all early running impurities were removed (~14 L). The column was then eluted with 10% MeOH/water and the eluate collected from the column in fractions was analyzed by HPLC. The fractions containing >99% 2-CdA were pooled and concentrated to a small volume. The concentrated pool was stored overnight at 5° C. to allow crystallization. The crystals were filtered, washed with water and dried under reduced pressure. The yield of the product (99% by HPLC) is 27% (17.4 g). This is approximately ten fold (1000%) greater than the methods reported in U.S. Pat. No. 5,208,327.

The identity of the product was established by using well known analytical methods. The analytical data is listed below: UV max 294 nm, $\epsilon$14749 (0.1 mg/mL in 0.1M NaOH aq); MS FAB MS, m/z 286.1 [M+H]+, HR FAB MS [M+Na]+ Expected 308.05267; Found 308.0522; NMR 1H (, ppm) 8.4 (1H), 7.8 (2H), 6.3 (1H), 5.3 (1H), 4.9(1H), 4.4 (1H), 3.9 (1H), 3.6 (1H), 3.3 (2H), 2.6 (1H), 2.3 (1H); 13C (, ppm) 156.721, 152.889, 150.011, 139.736, 118.117, 97.892, 83.512, 70.653, 61.607, 39.8 (buried in DMSO solvent resonance); Reverse Phase HPLC-Novapak-C-18 column, 5% acetonitrile/water, 0.1 M TEA pH 7 [with acetic acid] buffer retention time 10.56 min.; Elemental Analysis: Calculated %C 42.04%H 4.23%N 24.51%Cl 12.41; Found %C 41.71%H 4.33%N 24.31%Cl 12.78

EXAMPLE 3

Synthesis of 2-chloro-2'-deoxyadenosine using $CuCl_2$ as Metal Halide Lewis Acid DAPD (5 g, 18.8 mmol) is suspended in 425 mL dichloroethane/DMSO (4:1) and cooled to 0° C. under an inert atmosphere. To this is added Copper (II) chloride (9 g, 66.9 mmol) and tert-butyl nitrite (4.6 ml, 4.0 g, 38.6 mmol) and stirred while allowing the reaction to warm to room temperature. The reaction was stirred for 4 days and quenched with triethylamine. The reaction mixture was evaporated to dryness and the residue dissolved in sodium bicarbonate solution and purified by column chromatography. The product containing fractions were pooled together and evaporated to dryness the solid was recrystallized from water to give crystalline product. The overall yield of 2-CdA from starting material is 20% (0.9 g). The product was identified by HPLC [Novapak C-18; 5% acetonitrile/water, 0.1M TEA, pH 7 with acetic acid]; it comigrated with a coinjected sample of 2-CdA. This reaction establishes that metal halides of various compositions, so long as they are Lewis acids, work in the methods of the present invention.

EXAMPLE 4

Synthesis of 2-chloro-2'-deoxyadenosine using Pentyl Nitrite

DAPD (1 g, 0.375 mol) was suspended in dichloroethane (70 mL)/DMSO (15 mL) (~4:1) and cooled to less than 10° C. under an inert atmosphere. To this was added antimony trichloride (1.2 g, 0. mol) and pentyl nitrite (2.73 g, 3.1 mL, 0.0233 mol) and stirred while allowing the reaction to warm to room temperature. After 4 hrs the reaction was 19.2% complete by peak area on HPLC [Phenosphere 5 $\mu$M ODS2; 8% acetonitrile/water, 0.025M $KH_2PO_4$, pH 3]. An additonal 4 equivalents of pentyl nitrite (1.82 g, 2.06 mL, 0.0155 mol) was added. The reaction was stirred overnight and was quenched with triethylamine. The overall conversion to product was 31% by HPLC. The reaction product was confirmed by HPLC by coinjection with a standard sample.

EXAMPLE 5

Synthesis of 2-chloro-2'-deoxyadenosine in dichloroethane/dimethylformamide

DAPD (2 g, 7.5 mmol) was suspended in 170 mL dichloroethane/DMF (4:1) and cooled to 0° C. under an inert atmosphere. To this was added antimony trichloride (3.8 g, 10.5 mmol) and tert-butyl nitrite (1.85 ml, 1.6 g, 15.5 mmol) and stirred while allowing the reaction to warm to room temperature. Analysis of the reaction mixture by HPLC [Novapak C-18; 5% acetonitrile/water, 0.1M TEA, pH 7 with acetic acid] revealed product formation, confirmed by comigration with a coinjected 2-CdA standard. This experiment establishes that polar aprotic solvents other than DMSO can be used in the methods of the invention.

EXAMPLE 6

Synthesis of 2-chloro-2'-deoxyadenosine in Dichloromethane/DMSO

DAPD (2 g, 7.5 mmol) was suspended in 170 mL dichloromethane (DCM)/DMSO (4:1) and cooled to 0° C. under an inert atmosphere. To this was added antimony trichloride (3.8 g, 10.5 mmol) and tert-butyl nitrite (1.85 ml, 1.6 g, 15.5 mmol) while stirring while the reaction was allowed to warm to room temperature. Analysis by HPLC (Novapak C-18; 5% acetonitrile/water, 0.1M TEA, pH 7 with acetic acid) revealed product formation, which was confirmed by comigration of a product peak with a coinjected 2-CdA standard.

EXAMPLE 7

Determination of Optimal Solvent Combination

The syntheses were performed as in Example 1, except that the ratio of the two solvents was varied and the reactions were periodically monitored by HPLC [Novapak C-18; 5% acetonitrile/water, 0.1M TEA, pH 7 with acetic acid]. The results are presented in Table 1, below. The time vs. concentration of product 2-CdA and starting material DAPD suggested that a 1:10 to 10:1 ratio of the polar aprotic to nonpolar chlorinated is optimal for these reactions, with a 1:4 ratio being most optimal.

| DMSO/ | Time of Reaction (hours) | | | | |
| --- | --- | --- | --- | --- | --- |
| DCE Ratio | 16 | 22 | 40 | 72 | 120 |
| 100/0 | 17.2 | 15.9 | | | |
| 10/1 | 20.1 | 23.3 | | | 19.2 |
| 1/1 | 30.4 | 36.7 | 35 | | 36.3 |

-continued

| DMSO/ | Time of Reaction (hours) | | | | |
|---|---|---|---|---|---|
| DCE Ratio | 16 | 22 | 40 | 72 | 120 |
| 1/4 | 18.3 | | 57.3 | | |
| 1/10 | 27.7 | 25.9 | | | 14.4 |

EXAMPLE 8

Synthesis of 2-chloroadenosine

Diaminopurine ribonucleoside ("DAPR") (1.0 g, 3.54 mmol) was suspended in 80.0 mL dichloroethane/DMSO (4:1) and was cooled to less than 10° C. under an inert atmosphere. To this was added antimony trichloride (1.14 g, 5.01 mmol) and tert-butyl nitrite (0.872 ml, 7.4 mmol) and stirred while allowing the reaction to warm to room temperature. Analysis by HPLC (Phenosphere 5 $\mu$M ODS2; 8% acetonitrile/water, 0.025M $KH_2PO_4$, pH 3) showed a new peak around 15 min with concomitant loss of starting material DAPR. The reaction was stirred overnight and was quenched with triethylamine. The total conversion by HPLC was 23%. The product was identified by coinjection with pure 2-chloroadenosine obtained from Sigma Chemical Company, St. Louis, Mo.

EXAMPLE 9

Synthesis of 2-chloroadenine

Diaminopurine Hydrochloride [DAP] (2 g, 7.5 mmol) was suspended in 170 mL dichloroethane/DMSO (4:1) and cooled to 0° C. under an inert atmosphere. To this was added antimony tribromide (3.8 g, 10.5 mmol) and tert-butyl nitrite (1.85 mL, 1.6 g, 15.5 mmol) followed by stirring while allowing the reaction to warm to room temperature. Analysis by HPLC [Novapak C-18; 5% acetonitrile/water, 0.1M TEA, pH 7 with acetic acid] revealed a new peak that eluted at 5.59 minutes with concomitant loss of DAP starting material. The reaction was stirred overnight and quenched with triethylamine. HPLC showed new peak indicating the synthesis of 2-chloroadenine.

A sample of 2-chloro-2'-deoxyadenosine was taken and subjected to well-established deglycosylation conditions to give a mixture of both 2-chloroadenine and 2-chloro-2'-deoxyadenosine. This sample when co-injected with the reaction mixture from the previous Example showed overlapping peaks at 5.59 min verifying the formation of 2-chloroadenine. The product, 2-chloroadenine also appears at 8.78 min by HPLC in the Phenosphere 5 $\mu$M ODS2; 8% acetonitrile/water, 0.025M $KH_2PO_4$, pH 3 system.

This Example, along with the other Examples set forth herein, establish the generality of the halogenation reaction of the invention, such that any substituted or unsubstituted 2-halo-6-aminopurine can be produced from the corresponding substituted or unsubstituted 2,6-diaminopurine.

EXAMPLE 10

Synthesis of 2-bromo-2'-deoxyadenosine

DAPD (2 g, 7.5 mmol) was suspended in 170 mL dichloroethane/DMSO (4:1) and cooled to 0° C. under an inert atmosphere. To this was added antimony tribromide (3.8 g, 10.5 mmol) and tert-butyl nitrite (1.85 mL, 1.6 g, 15.5 mmol) followed by stirring while allowing the reaction to warm to room temperature. Analysis by HPLC [Novapak C-18; 5% acetonitrile/water, 0.1M TEA, pH 7 with acetic acid] revealed a new peak that eluted at 5.59 minutes (a retention time that was expected for the brominated product) with concomitant loss of DAPD starting material. The reaction was stirred overnight and quenched with triethylamine. The conversion by HPLC was 26% indicating the synthesis of 2-bromo-2'-deoxyadenosine.

EXAMPLE 11

Synthesis of 2-fluoro-2'deoxyadenosine

DAPD (2 g, 7.5 mmol) was suspended in 170 mL dichloroethane/DMSO (4:1) and cooled to 0° C. under an inert atmosphere. To this is added antimony trifluoride (1.88 g, 10.5 mmol) and tert-butyl nitrite (1.85 ml, 1.6 g, 15.5 mmol) followed by stirring while allowing the reaction to warm to room temperature. Analysis of the reaction mixture by HPLC [Novapak C-18; 5% acetonitrile/water, 0.1M TEA, pH 7 with acetic acid] revealed a new peak which eluted at 6.4 min, indicating the synthesis of 2-fluoro-2'-deoxyadenosine with concomitant loss of starting material. The reaction was stirred overnight and quenched with triethylamine. The conversion to product by HPLC was 8%.

The examples 1, 10 and 11 show the generality of the halogenation reaction by metal halides, such that any 2-halo substituted purine nucleosides can be produced from the corresponding 2,6-diamino nucleoside.

EXAMPLE 12

Synthesis of 2-chloro-2'-O-methyl-adenosine

2'-OMe-diaminopurine ribonucleoside (2 g, 6.7 mmol) was suspended in 152 ml dichloroethane/DMSO (4:1) and cooled to less than 10° C. under an inert atmosphere. To this was added antimony trichloride (2.14 g, 9.4 mmol) and tert-butyl nitrite (1.65 ml, 1.4 g, 14 mmol) followed by stirring while allowing the reaction to warm to room temperature. Analysis of the product mixture by HPLC [Novapak C-18; 5% acetonitrile/water, 0.1M TEA, pH 7 with acetic acid] revealed a new peak that eluted at 11.7 min with concomitant loss of starting material. The reaction was stirred overnight and quenched with triethylamine. The appearance of the new peak (51%), and disappearance of starting material, indicates the synthesis of 2-chloro-2'-O-methyl-adenosine, and establishes the generality of the method to 2'-substituted nucleosides as well as 2'-deoxynucleosides.

EXAMPLE 13

Preferred Stabilazation and Purification

A. Stabilization Column (Amberchrom Chromatography)

An Amberchrom CG161 XUS resin column (15 L) was prepared (~4 g 2-CldA per L of resin). Two-thirds of the resin was removed from the column and slurried with the reaction mixture and was then loaded onto the column. The column was washed with water until the absorbance at 265 nm drops below 5 or until the 2-CldA began to elute off the column and then 3 to 6 L fractions were collected. This was followed by elution with 5% methanol in water, and then with 30% methanol in water until the absorbance of the eluate at 265 nm was below 10. All fractions containing greater than 75% 2Cl-dA by peak area using HPLC were collected and concentrated on a rotary evaporator at 45° C. The collected fractions were concentrated to a gum, which was in a stable state and which could be left for up to 7 days without degrading.

B. Purification Column 1(Dowex Chromatography)

The gum from step A was dissolved in water and then concentrated to a concentration of 12–15 g of 2-CldA/L.

This solution was then charged onto a Dowex 1×4 anion exchange resin (1.3 L) column. The column was eluted first with water until the absorbance of the eluate at 265 nm was below 10, followed by 10% methanol in water, 15% methanol in water, and finally 25% methanol in water until all the 2-CldA had eluted off the column. Fractions containing 2-CldA were collected and assayed for purity by HPLC. The fractions that contained >90% pure 2Cl-dA (by HPLC) were adjusted to pH 7.5 or greater by using 1.0M sodium bicarbonate solution to achieve a concentration 10 mM sodium bicarbonate. These were saved individually, without pooling.

C. Purification Column 2 (Dowex Chromatography)

A second Dowex 1×4 anion exchange resin column (6 L) was prepared. (1 L of resin per 10 g of 2-CldA). The column was equilibrated in 10 mM sodium bicarbonate solution before the charge of 2-CldA was loaded. The charge was made up of the fractions from the 1×4 column in Step B. The fractions were loaded onto this 1×4 column in the order that they eluted off the first 1×4 column. After the column was loaded, the first eluant, 10 mM sodium bicarbonate in water, was started over the column. Once the majority of the 2-CldA was eluted off the column, the buffer was switched to 10% methanol in a 10 mM sodium bicarbonate solution. The column was washed with this eluant until 90% or more of 2Cl-dA had eluted off the column. All fractions that contained 2-CldA at greater than 98% purity by HPLC were concentrated in a rotary evaporator at 45° C. under vacuum.

D. Crystallization

The main (>98% pure) product pool was evaporated to a concentration of 22 g of 2-CldA per liter. The concentrated pool was filtered using a Buchner funnel and Whatman 54 hardened filter paper. The filtered solution was sealed and placed in a refrigerator for 17 hours at 8–14° C. for crystallization. The concentrated solution should remain at 8–14° C. for at least 14 hours. The crystallized 2-CldA was collected by filtration. The solids were washed with cold water. Both the solids and the filtrate were assayed for 2-CldA using HPLC.

E. Recrystallization 1

The solids from crystallization step D were redissolved in 10 mM sodium bicarbonate solution at approximately 4–5 grams of 2-CldA per L and were then concentrated down to 22 g/L using a rotary evaporator. The concentrated solution was then filtered and placed in the refrigerator for 17 hours for recrystallization. After 17 hours, the solids were filtered and both the solids and filtrate are assayed by HPLC.

F. Recrystallization 2

A significant amount of 2-CldA was detected in the filtrate from the recrystallization 1, step E, which was greater than 99% purity by HPLC. The filtrate was concentrated and recrystallized to recover 2-CldA. All the product that passed the 99% purity and the <0.1% impurity specifications were placed in a vacuum oven at a temperature of 37° C. for 24 hours to dry. After drying the crystals were ground up and dried until the water content was 2% or less. The crystals were weighed for a final yield.

For maximum recovery, fractions with <98% pure 2-CldA obtained from the Dowex Column 2, step C above, were pooled and reprocessed over a 1×4 Dowex column, using the same procedure as described in step C. The clean [>98%] fractions were combined with the filtrates from the recrystallizations. This solution was then concentrated and recrystallized as described above in step E.

What is claimed is:

1. A method for producing 2-halo-6-aminopurine-2',3'-derivatized nucleosides comprising the steps of:
    admixing a nonpolar aprotic organic solvent with a polar aprotic organic solvent to produce a solvent mixture;
    dissolving in said solvent mixture a nucleoside having the formula

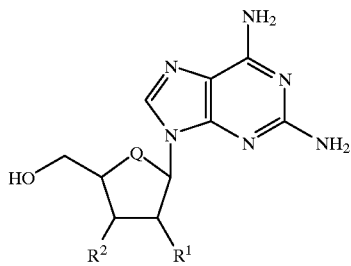

wherein Q is S;
   wherein $R^1$ and $R^2$ are a moiety with the formula O—A(Y)—O, wherein A is C, S, or P—R and wherein Y is O, S. N—R, or 2R;
   or wherein $R^1$ and $R^2$ are independently hydrogen, O—R, R, N—$R_2$, $N_3$, X, or S—R;
   wherein R is a linear or branched chain alkyl, cycloalkyl, alkoxyalkyl, ether, thioether, haloalkyl, aryl group, a monocyclic aryl group, a multicyclic aryl group, or a heterocyclic aryl group having from 1 to 20 carbon atoms and 1 to 10 heteroatoms, and X is Cl, Br, F, or I;
    reacting said nucleoside in said solvent mixture with an organic nitrite and a metal halide, wherein said metal halide is a Lewis acid, to produce a reaction product.

2. A method for producing 2-halo-6-aminopurine-2'-deoxy or 2'-substituted N-7 glycosylated nucleosides comprising the steps of:
    admixing a nonpolar aprotic organic solvent with a polar aprotic organic solvent to produce a solvent mixture;
    dissolving in said solvent mixture an unprotected N-7 glycosylated nucleoside having the formula

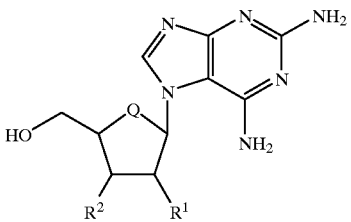

wherein Q is O or S;
   wherein $R^1$ and $R^2$ are a moiety with the formula O—A(Y)—O, wherein A is C, S, or P—R and wherein Y is O, S, N—R, or 2R;
   or wherein $R^1$ and $R^2$ are independently hydrogen, O—R, R, N—$R_2$, $N_3$, X, or S—R;
   wherein R is linear or branched chain alkyl, cycloalkyl, alkoxyalkyl, ether, thioether, haloalkyl, a monocyclic aryl group, a multicyclic aryl group, or a heterocyclic aryl group having from 1 to 20 carbon atoms and 1 to 10 heteroatoms, and X is Cl, Br, F, or I; and
    reacting said unprotected nucleoside in said solvent mixture with an organic nitrite and a metal halide, wherein said metal halide is a Lewis acid, to produce a reaction product.

* * * * *